United States Patent [19]
Kamei et al.

[11] Patent Number: 4,966,980
[45] Date of Patent: Oct. 30, 1990

[54] PROCESS FOR PRODUCING AZIRIDINES

[75] Inventors: Teruo Kamei, Yokohama; Yuuji Shimasaki, Takatsuki; Hideaki Tsuneki, Suita; Koichi Yamamoto, Tokyo; Yutaka Morimoto, Yokohama; Michio Ueshima, Takarazuka, all of Japan

[73] Assignee: Nippon Shokubai Kagaku Kogyo Co. Ltd., Osaka, Japan

[21] Appl. No.: 275,106

[22] PCT Filed: Mar. 12, 1988

[86] PCT No.: PCT/JP88/00262
§ 371 Date: Nov. 7, 1988
§ 102(e) Date: Nov. 7, 1988

[87] PCT Pub. No.: WO88/07038
PCT Pub. Date: Sep. 22, 1988

[30] Foreign Application Priority Data

Mar. 12, 1987 [JP] Japan .................. 62-55393
Mar. 12, 1987 [JP] Japan .................. 62-55394
Mar. 12, 1987 [JP] Japan .................. 62-55395
Jun. 25, 1987 [JP] Japan .................. 62-156617
Jul. 13, 1987 [JP] Japan .................. 62-172989
Oct. 9, 1987 [JP] Japan .................. 62-253868
Oct. 22, 1987 [JP] Japan .................. 62-265443

[51] Int. Cl.$^5$ ........................... C07D 203/02
[52] U.S. Cl. ................................. 548/954
[58] Field of Search ......................... 548/954

[56] References Cited

U.S. PATENT DOCUMENTS

| | | | |
|---|---|---|---|
| 3,369,019 | 2/1968 | Hamilton | 548/954 |
| 4,289,656 | 9/1981 | Hayes et al. | 502/311 |
| 4,301,036 | 11/1981 | Childress et al. | 520/254 |
| 4,337,175 | 6/1982 | Ramirez | 502/340 |
| 4,418,201 | 11/1983 | Williams | 548/579 |
| 4,477,591 | 10/1984 | Ramirez | 502/340 |

FOREIGN PATENT DOCUMENTS 227461 7/1987 European Pat. Off.
228898 7/1987 European Pat. Off.
230776 8/1987 European Pat. Off.

Primary Examiner—Nicholas S. Rizzo
Assistant Examiner—C. L. Cseh

[57] ABSTRACT

A process for producing an aziridine compound represented by the following general formula $$\underset{H}{\underset{N}{CH_2\diagdown\diagup CH-R}} \qquad (II)$$

wherein R represents hydrogen, or a methyl or ethyl group, which comprises intramolecularly dehydrating an alkanolamine represented by the following formula $$\underset{X\ \ \ Y}{CH_2-CH-R} \qquad (I)$$

wherein R is as defined, X is OH or $NH_2$, and Y is $NH_2$ when X is OH, and OH when X is $NH_2$, in the presence of a catalyst in the vapor phase in a reaction step (A) to form a reaction product containing the aziridine compound, and subjecting the reaction product to any one of the following procedures (1) to (3), (1) sending the reaction product to a recovery step (B) and recovering the aziridine compound in the presence of an amine compound,
(2) sending the reaction product to a distillation step (C) and distilling the aziridine compound in the presence of an amine compound, and
(3) sending the reaction product to the recovery step (B), recovering the aziridine compound in the presence of an amine compound, sending the recovered aziridine compound to the distillation step (C) and distilling it in the presence of an amine compound.

25 Claims, 1 Drawing Sheet

PROCESS FOR PRODUCING AZIRIDINES

[TECHNICAL FIELD]

This invention relates to a process for producing an aziridine compound, which comprises intramolecularly dehydrating an alkanolamine represented by the following general formula (I) in the vapor phase in the presence of a catalyst, and recovering the resulting aziridine of general formula (II) from the reaction product containing it in the presence of an amine compound.

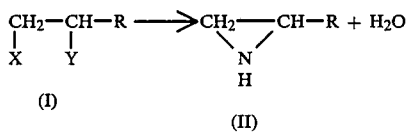

In the above reaction scheme, R represents hydrogen, or a methyl or ethyl group, X is OH or $NH_2$, and Y is $NH_2$ when X is OH, and OH when X is $NH_2$

[BACKGROUND ART]

The aziridine is a cYclic compound having a 3-membered ring with a large distortion. It has both ring-opening reactivity and the reactivity of an amine, and is useful as an intermediate for various compounds. In particular, ethylenimine has already gained widespread acceptance in the industry as a material for agricultural chemicals and pharmaceuticals and for amine-type polymers which are useful as textile treating agents.

A generally well-known method of producing an aziridine compound is typically a method of producing ethylenimine which comprises treating monoethanolamine sulfate in the liquid phase with a concentrated alkali solution, which has already been industrially practiced. This method, however, has many defects in industrial practice. For example, because of the need for using large amounts of sulfuric acid and an alkali as subsidiary materials, it has low productivity. Moreover, inorganic salts of low utilitarian value are formed as by-products.

In an attempt to remove the defects of aziridine production by such a liquid-phase method, various methods have been reported recently for the direct production of an aziridine compound by intramolecular dehydration reaction of an alkanolamine in the vapor phase in the presence of a catalyst without using subsidiary materials (U.S. Patents Nos. 4301036, 289656, 4337175 and 4477591, and European Laid-Open Patent Publications Nos. 227461, 228898 and 230776). These prior attempts, however, were directed mainly to catalysts for the intramolecular dehydration reaction in the vapor phase, and failed to propose an industrial process for obtaining the desired aziridine compound from the gaseous reaction product mixture.

In the production of an aziridine compound from an alkanolamine by the vapor-phase method, the reaction product gas contains by-products such as a carbonyl compound of the following general formula (III)

wherein R is as defined in formula (I) above, which corresponds to the starting alkanolamine, and various amines. If the starting alkanolamine is monoethanolamine, monoisopropanolamine or 2-amino-1-butanol, the corresponding carbonyl compound of formula (III) is acetaldehyde, acetone or methyl ethyl ketone, respectively. For example, U.S. Pats. Nos. 4,337,175 and 4,477,591 describe that in the production of ethylenimine from monoethanolamine, acetaldehyde is formed as a main by-product and monoethylamine and pyrazines are also formed as by-products. European Laid-Open Patent Publications No. 227,461, 228,898 and 230,776 also describe that the main by-products are the carbonyl compounds of formula (III) and various amines.

In the industrial production of organic compounds by a vapor-phase method, it is the general practice to recover the desired product from the vaporphase reaction product and purify it in order to obtain the final product. The industrial production of aziridine compounds from alkanolamines by the vapor-phase method, however, has the following problems. First of all, the aziridine compounds of formula (II) generally have a low boiling point and a very high vapor pressure. Moreover, they are very reactive, and liable to undergo polymerization and other reactions. Furthermore, among the various by-products formed in the vapor-phase method as mentioned above, the carbonyl compounds tend to react with the desired aziridine compounds and form adducts. Hence, the yield of the desired aziridine compounds is reduced. These problems should therefore be taken into consideration in producing aziridine compounds by the vapor-phase method.

[DISCLOSURE OF INVENTION]

It is an object of this invention to provide a process for producing an aziridine compound from an alkanolamine in the vapor-phase, in which the aziridine compound is efficiently recovered from the vapor-phase reaction product.

The present inventors made extensive investigations in order to achieve this object, and have found that it is very effective to carry out a recovery step and/or a distillation step in the presence of an amine compound.

Thus, according to this invention, there is provided a process for producing an aziridine compound represented by the following general formula

wherein R represents hydrogen, or a methyl or ethyl group, which comprises intramolecularly dehydrating an alkanolamine represented by the following formula

wherein R is as defined, X is OH or $NH_2$, and Y is $NH_2$ when X is OH, and OH when X is $NH_2$, in the presence of a catalyst in the vapor phase in a reaction step (A) to form a reaction product containing the aziridine compound, and subjecting the reaction product to any one of the following procedures (1) to (3), (1) sending the reaction product to a recovery step (B) and recovering the aziridine compound in the presence of an amine compound, (2) sending the reaction product to a distillation step (C) and distilling the aziridine compound in the presence of an amine compound, and (3) sending the reaction product to the recovery step (B), recovering the aziridine compound in the presence of an amine compound, sending the recovered aziridine compound to the distillation step (C) and distilling it in the presence of an amine compound.

The reaction step (A) of intramolecularly dehydrating the alkanolamine of formula (I) in the vapor-phase in the presence of a catalyst is described in the above-cited patent documents, and methods similar to those described there may also be used in this invention. For example, the alkanolamine is passed through a catalyst layer. If desired, the alkanolamine is diluted with an inert gas such as nitrogen to a suitable concentration, or in order to inhibit side reactions, ammonia, steam, hydrogen, etc. may be added to the starting gas. Alternatively, all inert gas may be replaced by ammonia. The operating pressure is atmospheric pressure or a reduced or elevated pressure. The reaction temperature is usually in the range of 300° to 500° C. The space velocity of the starting gas varies depending upon the type and concentration of the starting gas, the type of the catalyst, etc., but is generally within the range of 50 to 5,000 $hr^{-1}$. The catalyst may be those described in the above-cited patent documents. The silicon- or phosphorus-containing catalysts shown in European Laid-Open Patent Publications Nos. 227,461, 228,898 and 230,776 are preferred.

The characteristic feature of the present invention is that an aziridine compound is produced from the reaction product formed in the reaction step (A) by a treatment according to the above procedure (1), (2) or (3). The essential feature of the present invention is that in the production of the aziridine compound from the reaction product formed in the reaction step (A), the recovery step (B) and/or the distillation step (C) is carried out in the presence of an amine compound. The amine compound inhibits polymerization of the aziridine compound in the recovery step (B) and/or the distillation step (C), and enables it to exist stably. A problem arises in that a by-product carbonyl compound contained in the reaction product may react with the aziridine compound to form an adduct in the recovery step (B) and/or the distillation step (C). However when the amine compound exists, the by-product carbonyl compound reacts with the amine compound to form a stable adduct before it reacts with the aziridine compound. As a result, the amine compound produces the following effects.

(1) The decrease of the yield of the aziridine compound can be prevented.

(2) The decrease of the quality of the aziridine compound owing to the inclusion of the byproduct carbonyl compound can be prevented.

(3) The decrease of the stability of the aziridine compound can be prevented.

Various amine compounds can be used as the aforesaid amine compound in this invention. Primary amine compounds are particularly effective because they immediately react with the by-product carbonyl compound in the reaction product to form stable Schiff bases. Secondary amine compounds are also effective because they react with the carbonyl compound to form stable adducts. Specific examples of the amine compound include primary alkanolamines having 2 to 6 carbon atoms such as monoethanolamine and monoisopropanolamine; primary aliphatic amines having 2 to 8 carbon atoms such as ethylamine and ethylenediamine; primary aromatic amines having not more than 8 carbon atoms such as aniline; and secondary alkanolamines having not more than 8 carbon atoms such as diethanolamine and diisopropanolamine. Preferably, the amine compound is the same as the starting alkanolamine because it can be recovered with the unreacted starting material and recycled, and the process can be relatively simplified. Use of other amine compounds requires a recovery and re-use of the amine compound which has to be carried out independently of the recovery and re-use of the unreacted starting material. This complicates the process, and the amine compound is likely to be included in the product as an impurity.

The procedure (1) of sending the reaction product obtained in the reaction step (A) to the recovery step (B) to recover the aziridine compound of formula (II) in the presence of the amine compound will be described. If the unreacted alkanolamine in the reaction product obtained in the reaction step (A) exhibits a sufficient effect as the amine compound, the recovery step (B) may, if desired, be carried out by simply cooling the reaction product to condense and recover it. On the other hand, if the amount of the unreacted alkanolamine alone is insufficient to exhibit the effect of the amine compound, the reaction product obtained in the reaction step (A) is sent to recovery equipment where the aziridine compound of formula (II) is recovered in the presence of a sufficient amount of the amine compound In the latter case, it is convenient to use an absorption tower and feed the amine compound as an absorbing liquid, as is generally practiced.

When the amount of the unreacted alkanolamine is insufficient but the recovering step is carried out using water as the absorbing liquid without adding an additional supply of the amine compound, the aziridine compound undergoes polymerization. If an aqueous solution of sodium hydroxide is used as the absorbing liquid to prevent polymerization, the by-product carbonyl compound will react with the aziridine compound to form an adduct, and the yield of the aziridine compound will be decreased.

The amount of the amine compound to be present in the recovery step varies depending upon various factors such as the composition of the reaction product, the type of the amine compound, the temperature and the structure of the recovering device. Preferably, it is at least 0.1 mole per unit time per mole of the aziridine compound in the reaction product, and at least 1 mole per mole of the carbonyl compound. If it is too small, the stability of the aziridine compound is low, or the carbonyl compound does not sufficiently change to an adduct with the amine and the yield of the aziridine compound is decreased. An aqueous solution of the amine compound may be used as the absorbing liquid. If the viscosity of the amine compound is relatively high, the efficiency of contact of the amine compound with the reaction product can be increased by dissolving the amine compound in water and using the resulting solution of a low viscosity as the absorbing liquid. Volatilization of an amine compound having a relatively low boiling point may be inhibited by using it as an aqueous solution. Too much water in the absorbing liquid, however, induces the reverse reaction of the adduct of the carbonyl compound and the amine compound, and the carbonyl compound cannot be removed smoothly. Accordingly, when the amine compound is fed as an aqueous solution, the concentration of the amine compound in the absorbing liquid to be fed is preferably adjusted to at least 30 mole%, especially at least 80 mole%, although it may vary depending upon the water content of the reaction product. The temperature at which the aziridine compound is absorbed by the absorbing liquid is suitably within the range of 0° to 80° C. although it may vary depending upon the type of the absorbing liquid. The operating pressure may be atmospheric pressure or a reduced or elevated pressure. The absorption may be conveniently carried out by using an absorption tower. The absorption tower may be of a packed type, a tray type, a multitubular type, a spray type or a wetted wall, or of a combination of such types.

Now, the procedure (2) or (3) of sending the reaction product obtained in the reaction step (A) to the distillation step (C) where the aziridine compound of formula (II) is distilled in the presence of a sufficient amount of the amine compound will be described.

The liquid containing the aziridine compound obtained in the presence of the amine compound in the recovery step (B) is then sent to the distillation step (C) to distill the aziridine compound in the presence of the amine compound [Procedure (3)]. Alternatively, the liquid containing the aziridine compound obtained from the reaction product of the reaction step (A) without subjecting it to the recovery step (B) of the invention may be very effectively distilled in the presence of the amine compound according to this invention [Procedure (2)]. If the aziridine compound-containing liquid contains the amine compound such as the unreacted starting alkanolamine in an amount sufficient to produce the desired effect, no fresh supply of the amine compound may be required. If not, a fresh supply of the amine compound is added to the distillation system, and then the aziridine compound is distilled. Preferably, the amine compound is added by mixing it with the aziridine compound-containing liquid and feeding the mixture into a distillation tower. Alternatively, the amine compound may be separately fed into the distillation tower. Particularly, when water is present in the aziridine compound-containing liquid fed to the distillation tower, the amine compound is preferably added from above the material feeding tray of the distillation tower. This is effective for preventing formation of an adduct between the desired aziridine compound with the by-product carbonyl compound which is liberated by reverse reaction from the adduct of it with the amine compound owing to the presence of water near the material feeding tray and rises as a low-boiling component through the distillation tower. Because of the above manner of adding the amine compound, the amine compound is present in a sufficient amount above the material feeding tray and the amount of water there is decreased as a result of descending through the distillation tower as a high-boiling impurity. Hence, even when the by-product carbonyl compound is liberated, it is immediately converted back into an adduct with the amine compound, and the distillation step can be carried out without any substantial loss of the aziridine compound.

The amount of the amine compound to be present in the distillation tower may be properly selected depending upon the types and proportions of the compounds present in the distillation system, the amount of the carbonyl compound, etc. Preferably, it is at least 0.05 mole per mole of the aziridine compound fed into the distillation system, at least 1 mole, especially at least 5 moles, per mole of the carbonyl compound, and at least 1 mole per mole of water. If the amount of the amine compound is too small relative to the aziridine compound, its ability to inhibit polymerization of the aziridine compound is insufficient. If, on the other hand, the amount of the amine compound is too small relative to the carbonyl compound or water, the carbonyl compound is not fully converted to an adduct with the amine compound. As a result, there is a possibility that the yield of the aziridine compound will be decreased, the carbonyl compound will be included in the aziridine compound distillate, or the stability of the resulting aziridine compound will be reduced.

When the operation of distilling the aziridine compound is performed repeatedly several times, the distillation step (C) of this invention can be applied to any of such distillation operations.

The distillation may be carried out batchwise or continuously by any ordinary method properly chosen in a distillation tower of any type such as a packed tower or a plate tower. The operating pressure may be atmospheric, reduced or elevated pressure. The operating temperature may be properly determined depending upon the type of the aziridine compound, the stability of the adduct of the carbonyl compound and the amine compound, etc. Preferably, the temperature of the top of the distillation tower is in the range of 10° to 100° C. If the temperature is too high, the aziridine compound might be converted to another compound. If the temperature is too low, the cost of condensation in a heat-exchanger increases and the process becomes industrially disadvantageous. The above distillation can give the aziridine compound of a high purity in a high yield.

The process of this invention can be more conveniently carried out if in the reaction step (A), the alkanolamine of formula (I) is intramolecularly dehydrated in the vapor phase by passing it through the catalyst layer without substantially diluting it, preferably under a reduced pressure of 10 to 500 mmHg. When the alkanolamine is diluted with a diluting gas such as nitrogen and then reacted in the reaction step, the discharged gas at the time of recovering the reaction product in the recovery step still contains the desired product and the unreacted material, and the yield of the desired product may possibly be decreased. Furthermore, equipment is required for circulating the discharged gas or treating it to make it nontoxic. In contrast, if the starting alkanolamine is not substantially diluted prior to the reaction, the decrease of the yield of the desired aziridine compound can be prevented in the recovery step, and the large-scale discharged gas treating equipment can be omitted or simplified. Moreover, in this case, the reaction product may be directly introduced to the distillation step, and the recovery step can be omitted. The distillation operation can be carried out without a problem because no non-condensable gas exists. In the latter case, the reaction product is preferably passed through a cooler to cool it to a temperature suitable for the operation conditions of the distillation tower and then introduced into the distillation tower. In the distillation tower, it is separated into a fraction composed mainly of the aziridine compound and a distillation residue composed of the unreacted alkanolamine, water and other high-boiling impurities. As required, the fraction containing the aziridine compound as a main component obtained from the top of the distillation tower may be purified by further introducing it into a rectification column to obtain the aziridine compound of a higher purity. In the meantime, a mixture composed of the unreacted starting alkanolamine, the water formed and other high-boiling impurities is withdrawn from the bottom of the distillation tower. As required, the alkanolamine may be recovered from the mixture for reuse. Needless to say, in order to evaporate the starting alkanolamine smoothly or increase the activity of the catalyst, it is permissible to add such a small amount of nitrogen, ammonia, etc. as will not impair the aforesaid object of the invention in the reaction step.

[BEST MODE FOR CARRYING OUT THE INVENTION]

Figure 1:
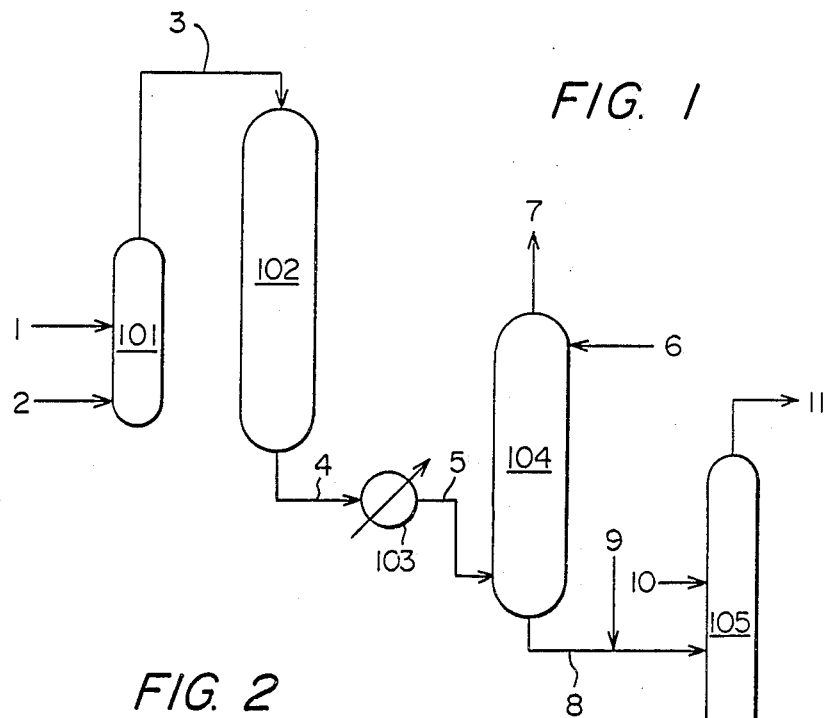
FIGS. 1 and 2 are flowsheets showing preferred embodiments of the present invention. The invention will now be described with reference to these drawings.

FIG. 1 illustrates a process for producing an aziridine compound comprising a reaction step, a recovery step and a distillation step.

The starting alkanolamine is fed into an evaporator 101 through a line 1, and gasified by heating. An inert gas such as nitrogen, helium or argon is fed into the evaporator 101 through a line 2 optionally together with ammonia, steam or hydrogen for inhibiting side reactions, and the concentration of the alkanolamine is adjusted. The starting gaseous mixture is then introduced into a vapor-phase dehydration reactor 102 filled with a catalyst via a line 3. The reactor 102 may be of a general fixed bed, fluidized bed or moving bed type. The reaction product which has left the reactor 102 comprises the aziridine compound, the unreacted alkanolamine, water, the carbonyl compound and amine compounds excepting the inert gas used as a diluent for the starting material. The reaction product is sent to a cooler 103 via a line 4 and cooled to a suitable temperature. After cooling, it is introduced into the lower portion of an absorption tower 104 via a line 5. A suitable packing is packed into the inside of the absorption tower 104, and from a line 6, an absorbing liquid composed of a liquid amine compound or its aqueous solution is fed from the upper part of the absorption tower 104 and brought into contact with the reaction product on the packing, and thereby absorbs the reaction product. The unabsorbed gaseous composition is discharged from the top of the absorption tower 104 via a line 7. The liquid which has absorbed the aziridine compound is withdrawn from the bottom of the tower via a line 8 and sent as a distillation feed material to a distillation tower 105 where it is distilled. This device is constructed such that if desired, the amine compound can be added to the starting material through a line 9, and the amine compound can also be introduced into the distillation tower through a line 10 provided above the material feeding tray. The carbonyl compound contained in the liquid which has absorbed the aziridine compound reacts with the amine compound to form a high-boiling adduct. The desired aziridine compound is obtained as a distillate from the top of the distillation tower 105 via a line 11. High-boiling compounds including water, the high-boiling adduct of the carbonyl compound and the amine compound and the added amine compound are withdrawn from the bottom of the tower through a line 12, and as required, the alkanlamine or the amine compound is recovered from the high-boiling compounds. If desired, the aziridine compound obtained from the line 11 is sent to a rectification tower and distilled again in the presence of the amine compound to obtain the aziridine compound of a higher purity.

Figure 2:
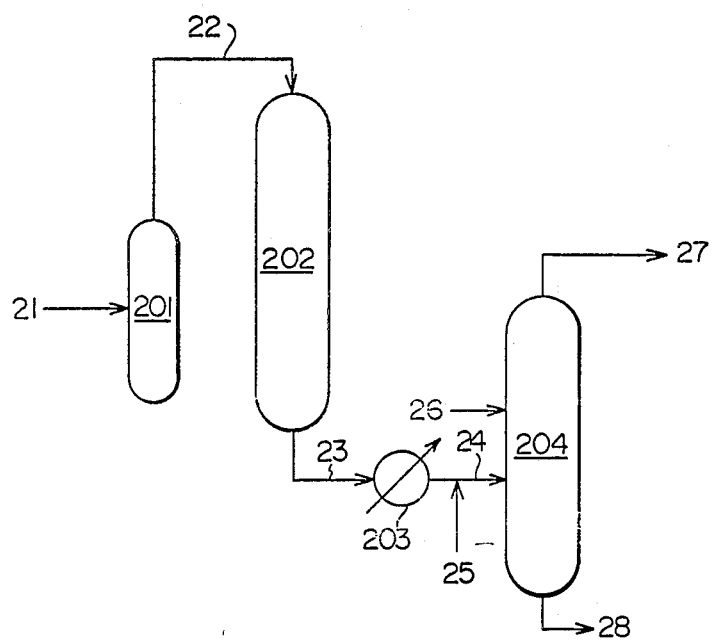

FIG. 2 illustrates an embodiment in which the alkanolamine is passed through a catalyst layer without being substantially diluted and intramolecularly dehydrated in the vapor phase in the reaction step, and the resulting reaction product is sent to the distillation step.

The starting alkanolamine is fed to an evaporator 201 via a line 21, and gasified by heating under reduced pressure. The gasified alkanolamine is introduced into a vapor-phase dehydrating reactor 202 via a line 22. The reaction product which has left the reactor 202 comprises an aziridine compound, the unreacted alkanolamine, water, the carbonyl compound and amine compounds. The reaction product is sent to a cooler 203 via a line 23 and cooled to a suitable temperature. It is then fed into a distillation tower 204 via a line 24 and distilled. This device is constructed such that as required, the amine compound can be added to the starting material through a line 25, or the amine compound can be introduced into the distillation tower through a line 26 provided above the material feeding tray. The carbonyl compound contained in the reaction product reacts with the amine compound to form a high-boiling adduct. As a result of distillation, the desired aziridine compound is obtained as a distillate via a line 27. High-boiling compounds containing water, the high-boiling adduct of the carbonyl compound and the amine compound, the unreacted alkanolamine and the added amine compound are withdrawn from the bottom of the distillation tower via a line 28, and as required, the alkanolamine or the amine compound is recovered from the high-boiling compounds. If desired, the aziridine compound obtained through the line 27 may be sent to a rectification tower, and distilled in the presence of the amine compound to obtain the aziridine compound having a higher purity.

The following examples illustrate the present invention more specifically. Analysis of the composition of the reaction product was carried out by gas chromatography with respect to the amine compound, the aziridine compound, the carbonyl compound and the amine-carbonyl compound adduct, and by using a Karl-Fischer water content meter with respect to water. The recovery ratio (%) of the aziridine recovered in the recovery step is defined as follows:

$$\text{Recovery ratio (\%)} = \frac{\text{the aziridine compound recovered (moles/hour)}}{\text{the aziridine compounds formed (moles/hour)}} \times 100$$

EXAMPLE 1

This example illustrates the process of this invention in accordance with procedure (1) using the apparatus of FIG. 1.

Preparation of a catalyst

A catalyst was prepared in accordance with Example 13 of European Laid-Open Patent Publication No. 227,461.

Silicon dioxide (300 g), 788.7 g of barium hydroxide octahydrate, 10.0 g of sodium hydroxide and 6.2 g of zirconium oxide were suspended in 3 liters of water.

With sufficient stirring, the suspension was heated and concentrated to give a white clay-like material. It was molded into solid cylindrical pellets having a diameter of about 5 mm and a length of about 5 mm. The pellets were dried, and then calcined at 600° C. for 2 hours to give a catalyst having the following composition $Si_{1.0}Ba_{0.5}Na_{0.05}Zr_{0.01}$ (by atomic ratio, excepting oxygen).

Dehydration reaction step (A)

Two hundred milliliters of the catalyst was filled in a stainless steel reaction tube having an inside diameter of 25 mm and set up in reactor 102, and heated to 390° C. by a heat medium. A starting gaseous mixture composed of monoethanolamine and nitrogen in a volume ratio of 10:90 was passed through the reaction tube at a space velocity of 1500 hr$^{-1}$ to react the monoethanolamine. Analysis showed that the reaction product contained 4.9% by volume of ethylenimine, 0.3% by volume of acetaldehyde, 3.6% by volume of monoethanolamine, 5.0% by volume of steam, 85.3% by volume of nitrogen and small amounts of ammonia and a dimerized product of monoethanolamine.

Recovery step (B)

The reaction product discharged from the reaction tube was cooled to 110° C. in cooler 103 and introduced into the lower part of absorption tower 104 consisting of a stainless steel tube having an inside diameter of 25 mm and a length of 1000 mm. The inside of the absorption tower 104 contained packings having a diameter of 3 mm (Dickson packings) packed to a layer height of 700 mm. Monoethanolamine as an absorbing liquid kept at 40° C. was fed into the absorption tower at a flow rate of 980 g/hour from its top via line 6, and brought into contact with the reaction product. The absorbing liquid which captured ethylenimine was withdrawn from the bottom of the absorption tower. The recovery ratio of ethylenimine was determined by analyzing the withdrawn liquid. It was thus ascertained that 99.6% of ethylenimine formed in the reaction step was absorbed by monoethanolamine. Acetaldehyde formed as a by-product in the reaction step did not exist in the above liquid, and the formation of N-ethylidene-1-hydroxyethylamine (the reaction product of acetaldehyde and the monoethanolamine used as the absorbing liquid) in an amount corresponding to the by-product acetaldehyde was determined.

EXAMPLES 2-6

These examples illustrate the process in accordance with procedure (1) using the apparatus of FIG. 1.

Example 1 was repeated except that the type, temperature and amount fed of the absorbing liquid were changed. The recovering conditions and the results are shown in Table 1.

EXAMPLE 7

This example illustrates the process in accordance with procedure (1) using the apparatus of FIG. 1.

Preparation of a catalyst

A catalyst was preapred in accordance with Example 3 of U.S. Pat. No. 4,477,591.

Niobium pentoxide (20 g) was dissolved in 200 ml of warm water with stirring. Aqueous ammonia was added to adjust the pH of the solution to 7.0. The precipitate formed was separated by filtration, washed with water, and dissolved in 320 ml of a 10% by weight aqueous solution of oxalic acid. Furthermore, 0.8 g of barium hydroxide octahydrate was added. Silicone carbide (240 cc) having a particle diameter of 5 mm was immersed in the solution, and the solution was evaporated to dryness, and calcined at 500° C. in an air current for 3 hours to give a supported catalyst containing 3.7% by weight of niobium pentoxide and 0.5% by weight of barium oxide ($Nb_{1.2}Ba_{0.1}O_{2.6}$).

Dehydration reaction step (A)

The dehydration reaction step of Example 1 was repeated except that the above catalyst was used and the reaction temperature was changed to 420° C. The reaction product was found to contain 2.1% by volume of ethylenimine, 0.7% by volume of acetaldehyde, 6.5% by volume of monoethanolamine, 2.5% by volume of steam, 87.3% by volume of nitrogen and small amounts of ammonia, ethylamine and a dimerized product of monoethanolamine.

Recovery step (B)

The reaction product was submitted to the recovery step in the same way as in Example 1. The recovering conditions and the results are shown in Table 1.

EXAMPLE 8

This example illustrates the process in accordance with procedure (1) using the apparatus of FIG. 1.

Preparation of a catalyst

A catalyst was prepared in accordance with Example 25 of European Laid-Open Patent Publication No. 230,776.

Aluminum nitrate nonahydrate (900 g) was dissolved in 2.4 liters of water, and a solution of 357.6 g of triammonium phosphate in 2.4 liters of water was added with stirring. The precipitate formed was separated by filtration and washed with water. Barium oxide (73.6 g) and 100 ml of water were added, and the mixture was well kneaded. The resulting clay-like material was molded into solid cylindrical pellets having an outside diameter of about 5 mm and a length of about 9 mm, dried and then calcined at 1000° C. for 2 hours to give a catalyst having the composition $Al_1P_1Ba_{0.2}$ (atomic ratio excepting oxygen).

Dehydration reaction step (A)

The same dehydration reaction step as in Example 1 was repeated except that the resulting catalyst was, used, the reaction temperature was changed to 420°C. and the starting gaseous mixture was changed to a mixture of monoisopropanolamine and nitrogen in a volume ratio of 20:80. The reaction product was found to contain 7.9% by volume of 2-methylethylenimine, 1.2% by volume of acetone, 8.0% by volume of monoisopropanolamine, 8.0% by volume of steam, 72.6% by volume of nitrogen and small amounts of ammonia and a dimerized product of monoisopropanolamine.

Recovery step (B)

The reaction product was submitted to the recover step and 2-methylethylenimine was recovered in the same way as in Example 1 except that monoisopropanolamine at 20° C. was used as the absorbing liquid, and fed at a rate of 2200 g/hour. The recovering conditions and the results are shown in Table 1.

EXAMPLE 9

This example illustrates the process in accordance with procedure (1) using the apparatus of FIG. 1.

Preparation of a catalyst

Cesium carbonate (114.0 g), 92.4 g of diammonium phosphate, 17.4 g of magnesium hydroxide, 26.6 g of thallium nitrate and 255.0 g of aluminum oxide were added to 2 liters of water, and concentrated by heating to give a white clay-like material. This material was molded into solid cylindrical pellets having an outside diameter of about 5 mm and a length of about 5 mm. The pellets were dried, and calcined at 600° C., in an air current for 2 hours to give a catalyst having the composition $Mg_{0.2}Cs_{0.7}P_{0.7}Tl_{0.1}Al_{5.0}$ (atomic ratio excepting oxygen).

Dehydration reaction step (A)

The same dehydration reaction step as in Example 1 was repeated except that the above catalyst was used, the reaction temperature was changed to 400° C., and the starting gaseous mixture was changed to a gaseous mixture consisting of 2-amino-1-butanol and nitrogen in a volume ratio of 20:80. The reaction product was found to contain 7.3% by volume of 2-ethylethylenimine, 1.4% by volume of methyl ethyl ketone, 9.1% by volume of 2-amino-1-butanol, 7.5% by volume of steam, 73.0% by volume of nitrogen and small amounts of ammonia and a dimerized product of 2-amino-1-butanol.

Recovery step (B)

The reaction product was subjected to the same recovery step as in Example 1 to recover 2-ethylethylenimine. The recovering conditions and the results are shown in Table 1.

decahydrate) was added. The mixture was aged for 1 hour while its pH was maintained basic by adding aqueous ammonia. The mixture was then cooled, and the precipitate was separated by filtration and washed with water to obtain a white solid. The solid was molded into solid cylindrical pellets having an outside diameter of about 5 mm and a length of about 5 mm, dried and then calcined at 500° C. in an air current for 2 hours to give a catalyst having the composition $Ca_{0.9}Na_{0.1}P_{0.5}$ (atomic ratio excepting oxygen).

Dehydration reaction step (A)

The same dehydration reaction step as in Example 1 was carried out except that 200 ml of the resulting catalyst was used, the reaction temperature was changed to 400° C., and the starting gaseous mixture was changed to a mixture composed of monoethanolamine and nitrogen in a volume ratio of 20:80. The reaction product gas was analyzed by gas chromatography, and it was determined that acetaldehyde formed in addition to ethylenimine as a main product.

Recovery step (B)

Subsequently, the reaction product was subjected to the same recovery step as in Example 1 to recover ethylenimine. Analysis showed that the liquid widhdrawn from the bottom of absorption tower 104 did not contain the acetaldehyde formed as a by-product in the reaction step (A), and the formation of N-ethylidene-1-hydroxyethylamine (the reaction product of acetaldehyde with the monoethanolamine used as the absorbing liquid) in an amount corresponding to the by-product acetaldehyde formed.

Distillation step (C)

The liquid withdrawn from the bottom of the absorption tower in the recovery step was fed into a site 0.6 m

TABLE 1

| Example | Aziridine compound:carbonyl compound in the reaction product gas | Absorbing liquid Type | Temperature (°C.) | Amount fed (g/hr) | Ratio of recovering the aziridine compound | Carbonyl compound in the absorbing liquid withdrawn from the bottom of the tower |
|---|---|---|---|---|---|---|
| 1 | Ethylenimine:acetaldehyde | Monoethanolamine | 40 | 980 | 99.9 | not detected |
| 2 | 4.9 vol. %:0.3 vol. % | Monoisopropanolamine (80% aq. sol.) | 20 | 980 | 99.9 | not detected |
| 3 | | Ethylenediamine | 20 | 980 | 99.7 | not detected |
| 4 | | n-Butylamine | 5 | 980 | 99.4 | not detected |
| 5 | | Aniline | 35 | 1500 | 99.6 | not detected |
| 6 | | Diethanolamine | 50 | 1700 | 99.3 | not detected |
| 7 | Ethylenimine:acetaldehyde 2.1 vol. %:0.7 vol. % | Monoethanolamine | 40 | 980 | 99.9 | not detected |
| 8 | 2-Methylethylenimine:acetone 7.9 vol. %: 1.2 vol. % | Monoisopropanolamine | 20 | 2200 | 99.8 | not detected |
| 9 | 2-Ethylethylenimine:methyl ethyl ketone 7.3 vol. %: 1.4 vol. % | Monoethanolamine | 40 | 980 | 99.6 | not detected |

EXAMPLE 10

This example illustrates the process in accordance with procedure (3) using the apparatus of FIG. 1.

Preparation of a catalyst

A catalyst was prepared in accordance with Example 7 of European Laid-Open Patent No. 228,898.

Calcium nitrate tetrahydrate (590.5 g) was dissolved in 1 liter of water, and while the solution was heated at 80° C. with stirring, 1 liter of an aqueous solution containing 537.0 g of disodium hydrogen phosphate (doabove the packed layer of stainless steel distillation tower having an inside diameter of 50 mm and a layer length of 2.4 m and packed with Dickson packings (6 mm), and continuously distilled at a reflux ratio of 4 under a tower top pressure of 200 mmHg. An ethylenimine reaction having a tower top temperature of 25° C. was obtained through line 11. The composition of the liquid fed into the distillation tower and the results obtained are shown in Table 2.

EXAMPLE 11

This example illustrates the process in accordance with procedure (3) using the apparatus of FIG. 1.

Example 10 was repeated except that ethylenediamine was used as the absorbing liquid in the recovery step (B) instead of the monoethanolamine, and the distillation device in the distillation step was one-fifth of the device used in Example 10 in scale. The composition of the liquid fed into the distillation tower and the results are shown in Table 2.

EXAMPLE 12

This example illustrates the process in accordance with procedure (3).

The reaction product gas discharged from the reaction step (A) of Example 10 was cooled to room temperature with cooling water, and then cooled to −30° C. using a cooling medium to condense the solution containing ethylenimine. Monoethanolamine was added to the condensed liquid, and the resulting solution was subjected to distillation in the same way as in Example 10. The composition of the solution fed to the distillation tower, and the results are shown in Table 2.

EXAMPLE 13

This example illustrates the process in accordance with procedure (3).

Monoethanolamine was added to the ethyleneimine fraction obtained by distillation in Example 10, and the resulting solution was distilled by the same operation as in Example 1. The composition of the solution fed into the distillation tower and the results are shown in Table 2.

EXAMPLE 14

This example illustrates the process in accordance with procedure (3) using the apparatus of FIG. 1.

Preparation of a catalyst

A catalyst was prepared in accordance with Example 14 of European Laid-Open Patent Publication No. 227,461.

Silicon dioxide (300 g), 132.8 g of strontium hydroxide octahydrate, 2.4 g of lithium hydroxide and 12.8 g of aluminum oxide were suspended in 1 liter of water. The suspension was concentrated by heating while the solution was fully stirred. The concentrated product was molded into solid cylindrical pellets having an outside diameter of about 5 mm and a length of about 5 mm, dried and calcined at 600° C. for 2 hours to give a catalyst having the composition $Si_1Sr_{0.1}Li_{0.02}A_{0.05}$ (atomic ratio excepting oxygen).

Dehydration reaction step (A)

The same dehydration reaction step as in Example 10 was carried out except that the resulting catalyst was used, the apparatus was reduced in scale to one-fifth of that used in Example 10, the heating temperature in the heat medium was changed to 400° C., and isopropanolamine was used instead of monoethanolamine. A gas-chromatographic analysis of the reaction product gas led to the determination of the presence of acetone in addition to 2-methylethylenimine as a main reaction product.

Recovery step (B)

2-Methylethylenimine, etc. in the reaction product gas discharged from the dehydration reaction step (A) were recovered in the same way as in Example 10 except that a recovery device of a smaller scale was used and isopropanolamine was used instead of monoethanolamine.

Analysis showed that the liquid withdrawn from the bottom of the absorption tower 104 did not contain acetone formed as a by-product in the reaction step, and 1-isopropylideneamino-2-propanol as the reaction product of acetone with the isopropanolamine used as the absorbing liquid was formed.

Distillation step (C)

The liquid withdrawn from the bottom of the absorption tower in the recovery step (B) was distilled in the same way as in Example 11 except that a distillation device of a smaller scale was used. The composition of the liquid fed into the distillation tower and the results are shown in Table 2.

TABLE 2

| | Liquid fed for the distillation tower | | | | | | | Aziridine compound fraction | | Yield of the aziridine compound (mole %) |
|---|---|---|---|---|---|---|---|---|---|---|
| | Composition (% by weight) | | | | Mole ratio* | | | Composition* (wt. %) | | |
| Example | Aziridine compound | Amine compound | Carbonyl compound | Water | Amine/ aziridine | Amine/ carbonyl compound | Amine/ water | Aziridine compound | Carbonyl compound | |
| 10 | Ethylenimine 4 | Monethanolamine 93.5 | Acetaldehyde 0.5 | 2 | 17 | 140 | 14 | above 99 | below 0.1 | 99 |
| 11 | Ethylenimine 4 | Monoethanolamine 10 Ethylenediamine 93.5 | Acetaldehyde 0.5 | 2 | 17 | 140 | 14 | above 99 | below 0.1 | 99 |
| 12 | Ethylenmine 28 | Monoethanolamine 56 | Acetaldehyde 4 | 12 | 1.4 | 10 | 1.4 | 98 | 0.5 | 97 |
| 13 | Ethylenimine 83.3 | Monoethanolamine 15 | Acetaldehyde 0.4 | 1.3 | 0.13 | 27 | 3.4 | above 99 | below 0.1 | 99 |
| 14 | 2-Methylethylenimine 4 | Isopropanolamine 93.5 | Acetone 0.5 | 2 | 18 | 145 | 11 | above 99 | below 0.1 | 99 |
| 17 | Ethylen- | Monoethanol- | Acet- | 11.3 | 1.7 | 23 | 1.5 | 98.3 | below 0.1 | 99 |

TABLE 2-continued

| Example | Liquid fed for the distillation tower | | | | | | | Aziridine compound fraction | | Yield of the aziridine compound (mole %) |
|---|---|---|---|---|---|---|---|---|---|---|
| | Composition (% by weight) | | | | Mole ratio* | | | Composition* (wt. %) | | |
| | Aziridine compound | Amine compound | Carbonyl compound | Water | Amine/ aziridine | Amine/ carbonyl compound | Amine/ water | Aziridine compound | Carbonyl compound | |
| | imine 24.6 | amine 60.0 | aldehyde 1.8 | | | | | | | |

*The carbonyl compound actually formed an adduct, but its amount was calculated as the monomer.

EXAMPLE 15

This example illustrates the process in accordance with procedure (2) using the apparatus of FIG. 2.

Dehydrating reaction step (A)

One liter of the catalyst prepared by the method of Example 8 was filled in a stainless steel reaction tube having an inside diameter of 25 mm and set up in reactor 202, and heated to 420° C. with a heat medium. Monoethanolamine was fed into evaporator 201, and gasified monoethanolamine was passed through the reaction tube at a space velocity of 1000 hr$^{-1}$ under a tube outlet pressure of 400 mmHg and continuously reacted. The reaction product was found to contain 67.6% by volume of monoethanolamine, 12.7% by volume of ethylenimine, 15.6% by volume of water, 1.35% by volume of acetaldehyde and small amounts of ammonia and a dimerized product.

Distillation step (C)

The reaction product obtained in the reaction step (A) was cooled to 100° C. in cooler 203, introduced into distillation tower 204 consisting of a stainless steel having an inside diameter of 50 mm and a height of 2000 mm at a site about ⅓ of the total length of the distillation tower from its top, and distilled at a reflux ratio of 4. The stainless steel tube contained Mcmahon packings having a diameter of 6.35 mm to a height of 400 mm in the concentrating portion and a height of 1200 mm in the recovery portion.

From the top of the distillation tower, ethylenimine having a purity of 98.1% by weight was obtained through line 27 at a rate of 291 g per hour. Water was almost the sole impurity. Acetaldehyde reacted with the unreacted monoethanolamine to form an adduct which was withdrawn from the bottom of the tower via line 28.

EXAMPLE 16

This example illustrates the process in accordance with procedure (2) using the apparatus of FIG. 2.

Dehydration reaction step (A)

The same dehydration reaction step as in Example 15 was carried out except that monoisopropanolamine was used instead of monoethanolamine, and gasified monoisopropanolamine was passed through the reaction tube at a space velocity of 200 hr$^{-1}$ under a tube outlet pressure of 60 mmHg. The reaction product was found to contain 9.9% by volume of monoisopropanolamine, 36.0% by volume of 2-methyl-ethylenimine, 40.1% by weight of water, 5.0% by volume of acetone, and small amounts of ammonia and a dimerized product.

Distillation step (C)

The reaction product obtained in the above reaction step (A) was introduced into the distillation tower in the same way as in Example 15. Monoisopropanolamine was fed into the distillation tower at a rate of 447 g/hour from an amine adding opening formed above the reaction product feed opening of the distillation tower. The reaction product was thus distilled at a reflux ratio of 8 under a pressure of 60 mmHg in the same way as in Example 15.

From the top of the distillation tower, 2-methylethylenimine having a purity of 97.8% by weight was obtained from line 27 at a flow rate of 335 g per hour. 98.1% of the 2-methylethyleneimine formed by the above reaction was recovered. Water is almost the only impurity. Acetone reacted with monoisopropanolamine to form an adduct, which was then withdrawn from the bottom of the tower through line 28.

EXAMPLE 17

This example illustrates the process in accordance with procedure (3) using the apparatus of FIG. 2.

Dehydration reaction step (A)

The same dehydration reaction step as in Example 15 was repeated except that the reaction pressure was changed from 500 mmHg to 100 mmHg and the space velocity was changed from 100 hr$^{-1}$ to 400 hr$^{-1}$. Analysis showed the reaction product to contain 42.4% by volume of monoethanolamine, 24.7% by volume of ethylenimine, 27.1% by volume of water, 1.8% by volume of acetaldehyde and small amounts of ammonia and a dimerized product of monoethanolamine.

Recovery step (B)

The reaction product discharged from the dehydration reaction step was first cooled to room temperature with cooling water and further to −10° C. with a cooling medium, and thus condensed and recovered to give a solution containing ethylenimine. Analysis showed that this solution did not contain acetaldehyde formed as a by-product in the reaction step, and the formation of N-ethylidene-1-hydroxyethylamine (the reaction product between acetaldehyde and the monoethanolamine used as the starting material) in an amount corresponding to the by-product acetaldehyde was determined.

Distillation step (C)

The solution obtained in the recovery step was fed into a distillation tower and distilled in the same way as in the distillation step in Example 15. From the top of the tower, ethylenimine having a purity of 98.3% was obtained at a rate of 267 g/hr in a yield of 99.0% based on the ethylenimine formed in the reaction step. The composition of the feed solution in the distillation tower and the results are shown in Table 2.

We claim:

1. A process for producing an aziridine compound represented by the following general formula

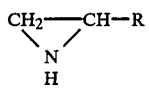

wherein R represents hydrogen, or methyl or ethyl group,
which comprises intramolecularly dehydrating an alkanolamine represented by the following formula

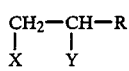

wherein R is as defined, X is OH or $NH_2$, and Y is $NH_2$
when X is OH, and OH when X is $NH_2$, in the presence of an intramolecular dehydration catalyst in the vapor phase in a reaction step (A) to form a reaction product containing the aziridine compound, by-product carbonyl compound and water, and subjecting the reaction product to any one of the following procedures (1) to (3), (1) sending the reaction product to a recovery step (B) and recovering the aziridine compound in the presence of at least 0.1 mole per unit time per mole of the aziridine compound in the reaction product and at least 1 mole per mole of carbonyl compound in the reaction product an absorbing liquid comprising of a primary or secondary amine compound, (2) sending the reaction product to a distillation step (C) and distilling the aziridine compound in the presence of at least 0.05 mole per mole of the axiridine compound fed into the distillation system, at least 1 mole per mole of the carbonyl compound and at least 1 mole per mole of water, of a primary or secondary amine compound, and (3) sending the reaction product to the recovery step (B), recovering the axiridine compound int he presence of at least 0.1 mole per unit time per mole of the aziridine compound in the reaction product and at least 1 mole per mole of the carbonyl compound, of an absorbing liquid comprising a primary or secondary amine compound, sending the recovered axiridine compound to the distillation step (C) and distilling it in the presence of a primary or secondary amine compound in an amount of at least 0.05 mole per mole of the axiridine compound fed into the distillation system, at least 1 mole per mole of the carbonyl compound and at least mole per mole of water.

2. The process of claim 1 wherein in the reaction step (A), the monoalkanolamine of formula (I) is reacted by passing it through a layer of the catalyst without being substantially diluted.

3. The process of claim 1 wherein in the reaction step (A), the monoalkanolamine of formula (I) is reacted by passing it through a layer of the catalyst without being substantially diluted, and then the reaction product is directly sent to the distillation step (C).

4. The process of claim 1 wherein in the distillation step (C), the amine compound is added from above the material feeding tray of the distillation tower.

5. The process of claim 1 wherein the amine compound is the starting alkanolamine of formula (I).

6. The process of claim 1 wherein the reaction product of step (A) is subjected to the procedure (1).

7. The process of claim 6 wherein the reaction product containing the axiridine compound from step (A) also includes a by-product carbonyl compound capable of reacting with the aziridine compound to form an adduct, and wherein the amine compound is added to the recovery step (B) in an amount to provide at least 0.1 mole of the amine compound per mole of the aziridine compound, and at least 1 mole of the amine compound per mole of the carbonyl compound.

8. The process of claim 1 wherein the reaction product from step (A) is subjected to the procedure (2).

9. The process of claim 8 wherein the reaction product from step (A) further includes a by-product carbonyl compound and water, and wherein the amine compound is added to the distillation step (C) in an amount sufficient to provide at least 0.05 mole of the amine compound per mole of the aziridine compound, and at least 1 mole of the amine compound per mole of the carbonyl compound, and at least 1 mole of the amine compound per mole of water.

10. The method of claim 9 wherein the amount of the amine compound is sufficient to provide at least 5 moles of the amine compound per mole of the carbonyl compound.

11. The process of claim 1 wherein the reaction product from step (A) is subjected to the procedure (3).

12. The process of claim 11 wherein the reaction product from step (A) further comprises a by-product carbonyl compound and water, and wherein the amine compound is present during the recovery step (B) in an amount of at least 0.1 mole per mole of the aziridine compound and at least 1 mole per mole of the carbonyl compound, and the amine compound is present in the distillation step (C) in an amount of at least 0.05 mole per mole of the aziridine compound in the distillation step, at least 1 mole per mole of the carbonyl compound and at least 1 mole per mole of water.

13. The process of claim 12 wherein the amount of the amine compound in the distillation step (C) is at least 5 moles per mole of the carbonyl compound.

14. The process of claim 1 wherein the intramolecular dehydration catalyst is a mixed metal oxide comprising an oxide of Si, P, Nb or Ta and at least one oxide of alkali metal and alkaline earth metal.

15. The process of claim 14 wherein the intramolecular dehydration catalyst comprises an oxide of tantalum or niobium and an oxide of an alkaline earth metal element.

16. The process of claim 14 wherein the intramolecular dehydration catalyst comprises an oxide of silicon or phosphorus and an alkali metal element and an alkaline earth metal element.

17. The process of claim 6 wherein the recovery step (B) comprises contacting the reaction product from step (A) with an absorbing liquid comprising said primary or seconddary amine compound and recovering the aziridine compound in the absorbing liquid.

18. The process of claim 17 wherein the absorbing liquid comprises an aqueous solution of said primary or secondary amine compound with the amount of the amine compound comprising at least 30 mole percent of the absorbing liquid.

19. The process of claim 11 wherein the recovery step (B) comprises contacting the reaction product of step (A) with an absorbing liquid comprising said primary or secondary amine compound, separating unabsorbed gases from the absorption liquid, and feeding the absorbing liquid containing the aziridine compound and the amine compound to the distillation step (C).

20. The process of claim 19 wherein the absorbing liquid comprises an aqueous solution containing at least 30 mole percent of the amine compound.

21. The process of claim 6 wherein the amine compound is the starting alkanolamine of formula (I).

22. The process of claim 8 wherein the amine compound is the starting alkanolamine of formula (I).

23. The process of claim 11 wherein the amine compound is the starting alkanolamine of formula (I).

24. The process of claim 3 wherein the amine compound is the starting alkanolamine of formula (I) and is added to the distillation step (C) from above the material feeding tray of the distallation tower.

25. The process of claim 1 wherein the primary or secondary amine has from 2 to 8 carbon atoms.

* * * * *

UNITED STATES PATENT AND TRADEMARK OFFICE
CERTIFICATE OF CORRECTION

PATENT NO. : 4,966,980

DATED : October 30, 1990

INVENTOR(S) : Teruo KAMEI, Yuuji SHIMASAKI, Hideaki TSUNEKI,
Koichi YAMAMOTO, Yutaka MORIMOTO, Michio UESHIMA It is certified that error appears in the above-identified patent and that said Letters Patent is hereby corrected as shown below:

Column 17, line 32, claim 1, after "product" insert --of--;

Column 17, line 33, claim 1, delete "of";

Column 17, line 37, claim 1, change "axiri-" to --aziri- --;

Column 17, line 43, claim 1, change "axiridine" to --aziridine--;

change "int he" to --in the--;

Column 17, line 49, change "axiridine" to --aziridine--;

Column 17, line 52, change "axiridine" to --aziridine--;

Column 18, line 6, claim 7, change "axiridine" to --aziridine--;

Column 18, line 60, claim 17, change "seconddary" to --secondary--;

Signed and Sealed this

Sixth Day of October, 1992

Attest:

DOUGLAS B. COMER

*Attesting Officer*     Acting Commissioner of Patents and Trademarks